Figure 1:
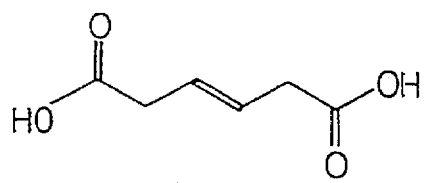
Figure 1:
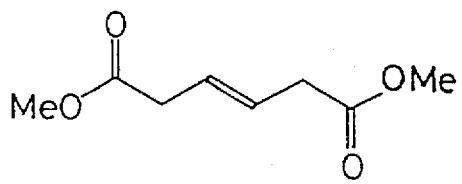
Figure 1:
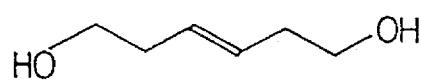
Figure 1:
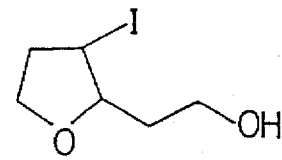
Figure 1:
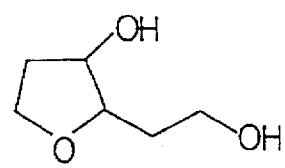
Figure 1:
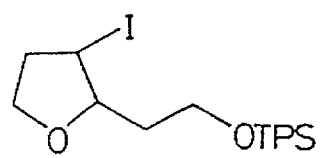
Figure 1:
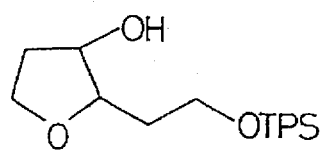
Figure 1:
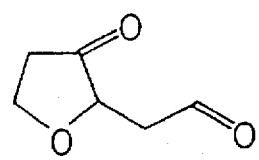
Figure 1:
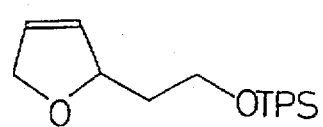
Figure 2:
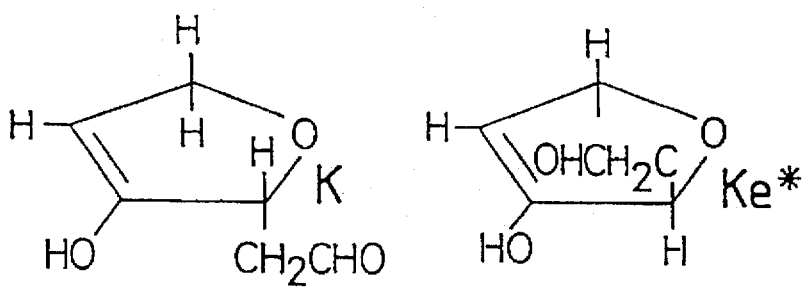
Figure 2:
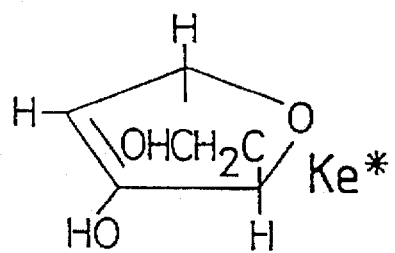
Figure 2:
Figure 2:
Figure 2:
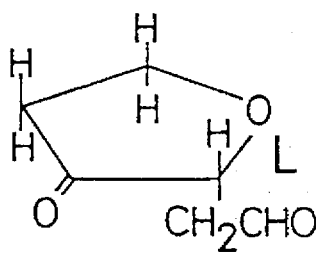
Figure 2:
Figure 2:
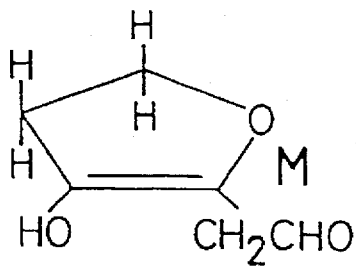

United States Patent [19]

Hendry

[11] Patent Number: 5,684,166

[45] Date of Patent: Nov. 4, 1997

[54] (-3-KETOTETRAHYDROFURAN-2-YL) ETHANAL DERIVATIVES AND A METHOD FOR THEIR PREPARATION

[75] Inventor: Neil Geddes Clarkson Hendry, Skene, United Kingdom

[73] Assignee: Biocure Limited, Aberdeen, Great Britain

[21] Appl. No.: 532,767

[22] PCT Filed: Mar. 22, 1994

[86] PCT No.: PCT/GB95/00579

§ 371 Date: Apr. 4, 1996

§ 102(e) Date: Apr. 4, 1996

[87] PCT Pub. No.: WO94/22849

PCT Pub. Date: Oct. 13, 1994

[30] Foreign Application Priority Data

Mar. 31, 1993 [GB] United Kingdom .................. 9306741

[51] Int. Cl.[6] ................................................ C07D 307/02
[52] U.S. Cl. ........................................................ 549/475
[58] Field of Search ........................................ 549/475

[56] References Cited

FOREIGN PATENT DOCUMENTS 0326826 8/1989 European Pat. Off. .

OTHER PUBLICATIONS

Pirrung et al., "Intramolecular Generation and [2,3]-Sigmatropic Rearrangement of Oxonium Ylides," J. Am. Chem. Soc. 1986,108, 6060–6042.

*Primary Examiner*—Amelia Owens

*Attorney, Agent, or Firm*—Heslin & Rothenberg, P.C.

[57] ABSTRACT

Compounds having utility in medicine in countering cellular malfunction e.g. in conditions embraced by the general term "cancer", which compounds normally exist us a keto-enol tautomeric pair, the racetalc keto form of which is rapresented by formula (Ia), wherein R is a hydrogen, lower alkyl, acyl, or another functional group of up to 6 carbons including at least one hetero atom, which atom may be directly bonded to the β-carbon, which compound may be in the acylic form shown or in a cyclic form as equilibrium keto-enol tautomer derivatives and anomeric forms thereof, including enantiomers when R is hydrogen and diastereoisomers when R is another group. A method of obtaining such a compound comprises selecting an appropriate dihydrofuran having a protected primary alcohol side chain in the 2-position, subjecting the said protected alcohol side chain-substituted dihydrofuran to oxidation using a chromium-based reagent to yield the corresponding acid, subjecting said acid to iodolaetonisation conditions to yield the cis,cis, trans-trisubstituted iodo-lactone which upon displacement of the iodine provides the cis,cis,cis-tri-substituted hydroxylacetone which is capable of being reduced to obtain a lactol which is in equilibrium with the corresponding open chain aldehyde.

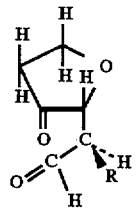

(Ia)

4 Claims, 2 Drawing Sheets

Compound 1

Compound 2

Compound 3

Compound 4

Compound 5

Compound 6

Compound 7

Compound 8

Compound 9

* e = enantiomer

(-3-KETOTETRAHYDROFURAN-2-YL) ETHANAL DERIVATIVES AND A METHOD FOR THEIR PREPARATION

This invention relates to novel compounds, methods of their preparation and medical uses thereof.

Although there have been many proposals for dealing with cellular malfunction e.g. in conditions embraced by the general term "cancer", these have usually involved surgery supplemented by a treatment e.g. chemo- or radiotherapy, which also causes some undesirable side effects such as hair loss, suppression of the immune system or other toxic effects. Thus in many cases, a patient's health can suffer significantly as a result of the treatment. There is an ever increasing need to find physiologically acceptable low-toxicity agents for use in medicine.

In other areas, post injury or surgery tissue regrowth may be unsatisfactory with excessive formation of scar tissue. A means of regulating the growth of tissue to minimise scar tissue formation would be desirable.

An object of the present invention is to obviate or mitigate the aforesaid disadvantages by providing compounds which have beneficial physiological effects and cell growth regulatory function.

According to this invention there are provided compounds of the formula (Ia) in which the compound normally exists as a keto-enol tautomeric pair, the racemic keto form of which is represented by the formula

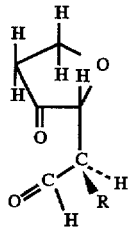

(Ia)

wherein R is a hydrogen, lower alkyl, acyl, or another functional group of up to 6 carbons including at least one hetero atom, which atom may be directly bonded to the β-carbon, which compound may be in the acyclic form shown or in a cyclic form as equilibrium keto-enol tautomer derivatives and anomeric forms thereof, including enantiomers when R is hydrogen and diastereoisomers when R is another group. Thus the group may be hydroxyl, a primary or secondary amine, amide, an acyl group, sulphur containing group etc.

Such formula (Ia) compounds are obtainable by a synthesis method be particularly described hereinafter with reference to the preferred compound which exists as a keto-enol tautomeric pair, the racemic keto form being of formula Ia where R=H i.e. (3-ketotetrahydrofuran-2-yl) ethanal and whilst not wishing to be bound by any theory, the attached scheme illustrates the equilibrium or molecular rearrangement relationships established between compounds of the invention (wherein R=H). However it must be emphasised that there may be parallel contributory intermediates or reaction steps not specifically identified in such an illustrative scheme. It will be appreciated that when R is hydrogen then various enantiomers are available but when R is not hydrogen a diastereomeric relationship is apparent between certain pairs of the compounds shown.

According to the invention compounds of therapeutic value are obtainable for example by subjecting trans-hexen-3-ene-1,6-diol to an iodo-etherification reaction to give the corresponding 3-iodotetrahydrofuran which retains the free α-hydroxyl which must be protected for subsequent reaction to displace the iodine yielding the cis 3-hydroxytetrahydrofuran which upon deprotection and Swern oxidation provides the desired racemic (3-ketotetrahydrofuran-2-yl)ethanal.

The same compounds can be derived by starting from an appropriate dihydrofuran having a protected primary alcohol side chain in the 2-position. Thus one route to these therapeutically active compounds is to subject the said protected alcohol side chain-substituted dihydrofuran to oxidation using a chromium-based reagent to yield the corresponding acid which in turn is subjected to iodolactonisation conditions to yield the cis, cis, trans-trisubstituted iodo-lactone which upon displacement of the iodine provides the cis, cis, cis-tri-substituted hydroxy-lactone capable of being reduced to obtain a lactol which is in equilibrium with the corresponding open chain aldehyde.

In this invention it is preferred that the α-hydroxyl is protected using a lipophilic tri-hydrocarbylsilyl derivative, e.g. using triisopropylsilyl chloride as reagent.

The invention will now be illustrated by way of example but it will be understood by those in the art that other variants of the method may be applied and other starting materials utilised without departing from the scope of the invention.

EXAMPLES

For ease of reference, the chemical structures of the starting material, intermediates and examples of the intended final products are given in a separate sheet at the end of this document. Each compound has been given a reference number which will be used in the discussion and the experimental details hereinafter.

Chemical synthesis of racemic (3-ketotetrahydofuran-2-yl) ethanal, Compound 8 (formula Ia above)

trans-β-Hydromuconic acid (compound 1) was esterified to give trans-β-hydromuconic acid dimethyl ester (compound 2) essentially quantitatively, using methanol under acidic catalysis. This was reduced to trans-hex-3-ene-1,6-diol (compound 3) with lithium aluminium hydride in 90% yield. The diol (compound 3) was subjected to an iodo-etherification reaction to give the trans-disubstituted tetrahydrofuran (compound 4) in 78% yield. The primary hydroxyl was converted to the corresponding lipophilic triisopropylsilyl derivative (compound 6) in 75% yield. The iodine was displaced using potassium superoxide, with inversion of configuration, to give the cis-disubstituted tetrahydrofuran (compound 7) in 17% yield. [Also obtained from this reaction was the mono-substituted dihydrofuran (compound 9) in 25% yield]. Compound 7 was deprotected to give the diol (compound 5) in 30% yield.

It will be demonstrated hereinbelow how one may convert both the diol (compound 5) and the silyl-protected derivative (compound 7) to the target molecule (compound 8) by oxidation under Swern conditions; that is oxalyl chloride, dimethyl sulphoxide, dichloromethane at −20° C. and later treatment with triethylamine.

Experimental Details 1 trans-β-Hydromuconic acid dimethyl ester, Compound 2 trans-α-Hydromuconic acid 1 (50.25 g, 0.349 mol) was dissolved in dry methanol (250 ml). Concentrated hydrochloric acid (2 drops) was added and the solution was heated under reflux for 4 hours. The solvent was evaporated in vacuo (at 40° C./10mm Hg) to give the diester as a pale yellow oil. The crude yellow compound was dissolved in diethyl ether (200 ml) and the solution washed with saturated sodium hydrogen carbonate solution (2×100 ml), water (2×100 ml), and brine (100 ml), dried (MgSO$_4$) and evaporated in vacuo to furnish Compound 2 as a very pale yellow oil (47.57 g, 80%)

$^1$H-NMR Spectrum (250,133 MHz) (CDCl$_3$) δ ppm from TMS 3.12 (4H, dd, J=5.4, 1.0 Hz 2×CH$_2$) 3.69 (6H, s, 2×OMe) 5.69 (2H, m, CH=CH) $^{13}$C-NMR Spectrum (62.512 MHz) (CDCl$_3$) δ ppm from TMS 37.5 (2×allylic C) 51.7 (2×C next to O) 125.8 (2×olefinic C) 171.9 (2×carboxy C)

2 trans-Hex-3-ene-1,6-diol Compound 3

The ester (compound 2) (10.4 g, 60.5 mol) dissolved in THF (30 ml) was added dropwise to a stirred suspension of LiAlH$_4$ (3.45 g, 90.9 mmol) in THF (250 ml) at ambient temperature. Stirring was continued for 1.5 hours. Sodium sulphate decahydrate (4.4 g) was added and stirring continued for a further 30 minutes. The mixture was filtered and the residue was washed with THF (4×200ml). Each wash entailed the residue being stirred vigorously in the solvent for at least 30 minutes. The washings were combined with the original flitrate, dried (MgSO$_4$) and evaporated under in vacuo to furnish crude trans-hex-3-ene-1, 6 diol (Compound 3) as a pale yellow oil (6.4 g, 55 mmol, 91% yield) suitable for use without further purification. The combined filtrates were evaporated under reduced pressure to give trans-hex-3-ene-1,6-diol (compound 3) as a colourless oil (0.65 g, 5.6 mmol, 90% yield).

$^1$H-NMR Spectrum: (250.133 MHz) (CDCl$_3$) δ ppm from TMS 2.25 (4H,m, allylic H) ca 2.8 (2H,s,OH) 3.64 (4H,m, H next to O) 5.50 (2H,m, olefinic H) $^{13}$C-NMR Spectrum: (62,512 MHz) (CDCl$_3$) δ ppm from TMS 35.8 (2×allylic C) 61.4 (2×C next to O) 129.3 (2×olefinic C) 171.9 (2×carboxy C) Mass Spectrum: CI (NH$_3$) m/z= 134 ( M+NH$_4^+$) 117 (M+H)

3 trans-2-(2-Hydroxyethyl)-3-iodotetrahydrofuran, Compound 4

The diol (compound 3) (120 mg, 1.03 mmol) was dissolved in acetonitrile (10 ml). Sodium hydrogen carbonate (0.83 g, 9.9 mmol) was suspended in the solution and the mixture was stirred at 0° C. for 10 minutes. iodine (0.78 g, 3.07 mmol) was added and stirring was continued at 0° C. for 6 hours. Sodium thiosulphate solution was added until the iodine colour disappeared and the mixture was extracted with diethyl ether (2×30ml). The organic extracts were combined, dried (MgSO$_4$), and evaporated in vacuo to furnish compound 4 (196 mg, 78%) as a yellow oil.

$^1$H-NMR Spectrum: (250,133 MHz) (CDCl$_3$) δ ppm from TMS 1.67 (1H, m, H not next to O) 2.09 (1H, m, H not next to O) ca2.2 (1H, bs, OH) 2.30 (1H, m, H not next to O) 2.54 (1H, m, H not next to O) 3.81 (3Hs, m, H next to O or I) 3.93 (2Hs, m, H next to O or I) 4.15 (1H, m, H next to O or I) $^{13}$C-NMR Spectrum: (62,512 MHz) (CDCl$_3$) δ ppm from TMS 23.1 (C not next to O) 34.7 (C not next to O) 38.1 (C next to I) 60.7 (C next to O) 67.3 (C next to O) 87.4 (C next to O) Mass Spectrum: CI(NH$_3$ ) m/z= 260 (M+NH$_4^+$) 243 (M+H$^+$) Infrared Spectrum: (KBr disc) v=3412(OH), 2941, 2879, 1734cm$^{-1}$ 4 trans-2(2-Triisopropylsilyloxyethyl)-3-iodotetrahydrofuran, Compound 6

Compound 4 (0.9 g, 4.1 mmol) and triisopropylsilyl (0.95 g, 5.0 mmol) were dissolved in N,N-dimethylformamide (DMF)(10 ml) at 0°. A solution of imidazole (0.6 g, 8.8 mmol) in DMF (5 ml) was added and the mixture was stirred for 24 hours during which the reaction was allowed to warm to ambient temperature. The mixture was poured into water (50 ml) and extracted with petroleum ether (50 ml). The organic layer was washed with water (2×50ml), dried over magnesium sulphate, filtered and evaporated in vacuo to give the near pure product. Flash column chromatography using ethyl acetate/petrol (5:95) as eluent gave the silyltetrahydrofuran (compound 6) (1.1 g, 75%)

$^1$H-NMR Spectrum (250.133 MHz) (CDCl$_3$) δ ppm from TMS 1.05 (21H, m, 3×C$_3$H$_7$) 1.65 (1H, m, H not next to O) 2.00 (1H, m, H not next to O) 2.31 (1H, m, H not next to O) 2.58 (1H, m, H not next to O) 3.72–4.05 (5H, m, Hs next to O or I) 4.21 (1H, m, H next to O or I) $^{13}$C-NMR Spectrum (62.512 MHz) (CDCl$_3$) δ ppm from TMS 12.2 (CHCH$_3$) 18.3 (CHCH$_3$) 24.2 (C not next to O) 36.4 (C next to I) 38.5 (C not next to O) 60.4 (C next to O) 67.0 (C next to O) 85.7 (C next to O) Mass Spectrum: CI(NH$_3$) m/z= 399 (M+H) 355 (M-C$_3$H$_7$) Infrared Spectrum: (KBr disc) v=2941, 2866, 1464, 1385, 1250, 1100 cm$^{-1}$ TLC Specifications: Plate: Silica 60F$_{254}$, 0.2 mm thickness, aluminium (Merck) Detection: Methanolic H$_2$SO$_4$ Solvent System: ethyl acetate/petrol (60–80) 1/1 Single Spot R$_f$=0.89

5 cis-2(2-(Triisopropylsilyloxy)ethyl)-3-hydroxytetrahydrofuran, Compound 7 and 2-(2-Triisopropylsilyloxy)ethyl-2,5-dihydrofuran, Compound 9

The silyl-protected iodofuranyl ethanol (compound 6) (1.01 g, 2.5 mmol) was dissolved in dry dimethyl formamide containing 18-crown-6 (50 mg). Potassium superoxide (0.32 g, 4.5 mmol) was added and the mixture was stirred under argon for 16 hours at room temperature. Water (30 ml) was added and the mixture was extracted with petroleum ether 60–80 (50 ml). The organic layer was washed with water (2×20ml), dried over sodium sulphate and evaporated in vacuo. The residue (0.84 g) was purified by loading onto a flash silica chromatography column which was eluted with petrol/acetone (4/1). Two compounds were isolated (R$_f$=0.8,0.4), the more polar of which was identified as alcohol 7, (122 mg, 17%), the less polar as dihydrofuran 9 (193 mg, 25%). $^1$H-NMR Spectrum (250,133 MHz) Compound 7 (CDCl$_3$) δ ppm from TMS 1.09 (21H, m, C$_3$H$_7$) 2.03 (4H, m, CH$_2$ not next to O) 3.77 (3H, m, Hs next to O) 3.91 (m, 1H, H next to O) 4.03 (m, 1H, next to O) 4.35 (m, 1H, next to O) $^{13}$C-NMR Spectrum (62.512 MHz) Compound 7 (CDCl$_3$) δ ppm from TMS 11.7 (CHCH$_3$) 17.8 (CH$_3$) 31.8 (C not next to O) 34.7 (C not next to O) 60.5 (C next to O) 66.0 (C next to O) 72; 0 (C next to O) 82.9 (C next to O) Mass Spectrum: Compound 7 CI (NH$_3$) m/z= 289 (M+H) 245 (M-C$_3$H$_7$) Infrared Spectrum: Compound 7 (KBr disc) v=3429(OH), 2941, 2866, 1641, 1464, 1385 cm$^{-1}$ TLC Specifications: Plate Silica 60F$_{254}$, 0.2 mm thickness, aluminium (Merck) Detection: Methanolic H$_2$SO$_4$ Solvent System: ethyl acetate/petrol (60–80) 1/1 Single Spot R$_f$=0.33 $^1$H-NMR Spectrum (250.133 MHz) Compound 9 (CDCl$_3$) δ ppm from TMS 1.00 (21H, m, 3×C$_3$H$_7$) 5 1.78 (2H, m, Hs not next to O) 3.82 (2H, m, Hs next to O) 4.62 (2H, m, allylic Hs, next to O) 4.96 (1H, m, allylic H, next to O) 5.86 (2H, m, olefinic Hs) $^{13}$C-NMR Spectrum (62,512 MHz) Compound 9 12.2 (3×CHCH$_3$) 18.3 (3×CH$_3$) 39.7 (C not next to O) 60.6 (C next to O) 75.0 (C next to O) 126.2 (olefinic C) 130.5 (olefinic C) Infrared Spectrum: (KBr disc) v=2941, 2890, 1464, 1251, 1084cm$^{-1}$ Mass Spectrum: CI (NH$_3$) m/z= 271 (M+H) 227 (M-C$_3$H$_7$) TLC Specifications: Plate Silica 60F$_{254}$, 0.2 mm thickness, aluminium (Merck) Detection: Methanolic $H_2SO_4$ spray Solvent System: ether/petrol (60–80) 3/2 Single Spot $R_f$=0.91

6 cis-2-(2-Hydroxyethyl)-3-hydroxytetrahydrofuran (Compound 5)

cis-2-(2(Triisopropylsilyloxy) ethyl)-3-hydroxytetrahydrofuran (Compound 7)(0.23 g, 0.80 mmol) was dissolved in tetrahydrofuran (20 ml) and treated with a 1M solution of tetrabutylammonium fluoride in tetrahydrofuran (1 ml, 1 mmol) and set aside at room temperature for 24h. The reaction mixture was evaporated in vacuo and the residue purified by flash column chromatography (petrol/acetone 1/1). The desired diol (Compound 5) was isolated as a colourless oil (0.08 g, 76%) $^1$H NMR Spectrum (250,133 MHz) (CDCl$_3$) δ ppm from TMS 1.94 (3H,m, Hs not next to O) 2.19 (1H,m,H not next to O) ca2.8 (2H,OH) 3.67–3.89 (4H,m, Hs next to O) 4.03 (1H,m,H next to O) 4.30 (1H,m,H next to O) $^{13}$C-NMR Spectrum: (CDCl$_3$) δ ppm from TMS 31.1 (C not next to O) 35.0 (C not next to O) 60.1 (C next to O) 66.0 (C next to O) 72.5 (C next to O) 82.6 (C next to O) Infrared Spectrum: (KBr disc) v=3377, 2949, 2883, 2241, 1703, 1440, 1062cm$^{-1}$ Mass Spectrum: CI (NH$_3$) m/z= 150 (M+NH$_4$) 133 (M+H) TLC Specifications: Plate Silica 60F$_{254}$, 0.2 mm thickness, aluminium (Merck) Detection: Ethanolic H$_2$SO$_4$ spray Solvent System: petrol/acetone, 1/1 Single spot $R_f$=0.05

7 Preparation of (3-Ketotetrahydrofuran-2-yl)ethanal (Compound 8)

A solution of DMSO (0.18 ml, 2.67 mmol) in dichloromethane (2 ml) was added to a stirred solution of oxalyl chloride (0.12 ml, 1.4mmol) under argon at –60° C. After 2 minutes a solution of the diol (Compound (0.07 g, 0.53 mmol) in dichloromethane (2 ml) was added and the stirring was continued for 40 minutes. N,N-Diisopropylethylamine (0.8 ml, 5.7 mmol) was added. The mixture was allowed to attain room temperature. The volatile components were evaporated under reduced pressure at room temperature. The residue was applied to a flash silica column and eluted with petrol (60–80)/acetone 3/2 to give a pale yellow oil (47 mg).

$^1$H-NMR Spectrum (250.133 MHz) (CDCl$_3$) δ ppm from TMS 9.71 (1H,m) 4.36 (1H,dt,J=4Hz, 11Hz) 4.10 (1H,m) 4.04 (1h, m) 3.00 (1H,ddd,J=0.5Hz,4Hz,18Hz) 2.85 (1H, ddd,J=1Hz,7Hz,19Hz) 2.73 (1H,m) 2.53 (2H,m) $^1$H-1NMR Spectrum (250.133 MHz) (D$_2$O) δ ppm from TMS 9.59 (s) 5.66 (m) 5.19 (t,J=5.8Hz) 3.8–4.4 (m) 1.8–3.2 (m) $^{13}$C-NMR Spectrum: (D$_2$O) δ ppm from TMS 22.1 25.4 39.3 40.8 40.9 41.1 41.8 47.5 50.2 67.8 70.6 70.7 79.7 87.5 87.6 90.8 97.3 102.9 103.3 116.0 117.8 167.0 223.1 $^{13}$C-DEPT135-NMR Spectrum: (D$_2$O) δ ppm from TMS 22.1 (–) 25.4 (–) 39.3 (+) 40.8 (+) 40.9 (+) 41.1 (+) 41.8 (+) 47.5 (–) 50.2 (–) 67.8 (+) 70.6 (+) 70.7 (+) 79.7 (–) 87.5 (–) 87.6 (–) 102.9 (–) 103.3 (–) (+) Denotes a positive peak and (–) denotes a negative peak.

In this DEPT135 spectrum CH$_3$ and CH resonances constitute one group of peaks, CH$_2$ resonances comprise a second group and quaternary carbons are not shown. It is the convention for the CH$_3$ and CH resonances to be positive and for the CH$_2$ resonances to be negative. In this spectrum the assignment of an individual peak could not be made and so the absolute (+) or (–) assignments are arbitrary but the relative assignments are correct.

The NMR spectra in water are extremely complicated. This is thought to be due to the formation in aqueous solution of an equilibrium mixture of several isomers of the parent compound $^{13}$C-NMR Spectrum: (D$_6$-Benzene) δ ppm from TMS 20.1 22.6 30.2 36.1 44.9 64.8 74.5 96.5 162.1 197.7 205.0 Infra Red Spectrum: Thin film v=1757,1719, 1157,1093,1061cm$^{-1}$ TLC Specifications: Plate: Silica 60F$_{254}$, 0.2 mm thickness, aluminium (Merck) Detection: Ethanolic H$_2$SO$_4$ spray Solvent System: dichloromethane:acetone 1:1 R$_f$=0.67

Substances having the structures of the synthesised target material when added to in vitro cultures of various cancer cell lines produced a dose-related cell death as indicated in the Tables below.

TABLE I

| Cell Line | Cell No (% Control) | | | | | |
|---|---|---|---|---|---|---|
| Dose (μg/ml) | Control | 0.5 | 1.0 | 1.5 | 2.0 | 5.0 |
| HeLa | 14498 | 12165 | 10932 | 7453 | 4675 | 201 |
|  | (100) | (83.9)** | (75.4)** | (51.4)** | (32.2)** | (1.4)** |
| MOLT4 | 4978 | 4543 | 3920 | 2674 | 1701 | 619 |
|  | (100) | (91.2)** | (78.8)** | (53.7)** | (34.2)** | (12.4)** |
| WIL2 | 9880 | 8431 | 5810 | 2459 | 1591 | 705 |
|  | (100) | (85.3)** | (58.8)** | (24.9)** | (16.1)** | (7.1)** |
| PA-1 | 13369 | 11346 | 11276 | 10338 | 9678 | 2729 |
|  | (100) | (84.3)** | (84.9)** | (77.3)** | (72.4)** | (20.9)** |

TABLE II

| Cell Line | Cell No (% Control) | | | | | |
|---|---|---|---|---|---|---|
| Dose (μg/ml) | Control | 2.0 | 5.0 | 7.5 | 10.0 | 20.0 |
| KNOS/NP | 11168 | 9442 | 6356 | 2469 | 862 | 380 |
|  | (100) | (84.5)** | (56.9)** | (22.1)** | (7.7)** | (3.4)** |
| CaSki | 4939 | 4401 | 4617 | 3495 | 2800 | 234 |
|  | (100) | (89.1)** | (93.5) | (70.8)** | (56.7)** | (4.7)** |
| PC3 | 6725 | 5908 | 4532 | 2211 | 627 | 399 |
|  | (100) | (87.9)* | (67.4)** | (32.9)** | (9.3)** | (5.9)** |
| WiDr | 6427 | 5845 | 5762 | 5097 | 3826 | 178 |

TABLE II-continued

| Cell Line | Cell No (% Control) | | | | | |
|---|---|---|---|---|---|---|
| Dose (µg/ml) | Control | 2.0 | 5.0 | 7.5 | 10.0 | 20.0 |
| G361 | (100) 4685 (100) | (90.9)* 1679 (35.8)** | (89.6)* 314 (6.7)** | (79.3)** 159 (3.4)** | (59.5)** 142 (3.0)** | (2.8)** 230 (4.9)** |

Stat. sig.
* P < 0.05
**P < 0.001
HeLa = Human cervical carcinoma
MOLT4 = Human T-cell leukaemia
WIL2 = Human B lymphoblastoma
PA-1 = Human ovarian teratocarcinoma
KHOS/NP = Human osteocarcinoma
CaSki = Human cervical epidermoid carcinoma
PC3 = Human prostate adenocarcinoma
WiDr = Human colon adenocarcinoma
G361 = Human malignant melanoma The compounds of the invention may possess inherent activity or may be activated within the body by e.g. Macrophage or liver microsomes.

Therapeutic use of these materials is contemplated following usual trials, and delivery may take the usual forms by being formulated with, as necessary, pharmaceutically acceptable auxiliaries, vehicles, extenders, excipients, gelling agents etc. into suitable oral dosage forms such as, tablets, pills, capsules, powders, topical formulations such as creams, gels, sprays etc. and other administrable forms such as suspensions or solutions for transdermal, intramuscular or other injectable formulations. Applications are in tumour regression therapy, scar tissue suppression and stimulus of the immune system to influence cellular malfunction.

I claim:

1. A compound of the formula (Ia) in which the compound normally exists as a keto-enol tautomeric pair, the racemic keto form of which is represented by the formula

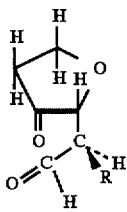

(Ia)

wherein R is a hydrogen, hydroxyl, lower alkyl, acyl, or another functional group of up to 6 carbons including at least one hetero atom, which atom may be directly bonded to the β-carbon.

2. A compound according to claim 1 wherein the functional group is a primary or secondary amine, amide, an acyl group, or sulphur containing group.

3. A method of obtaining (3-ketotetrahydrofuran-2-yl)ethanal comprising subjecting trans-hexen-3-ene-1,6-diol to an iodo-etherification reaction to give the corresponding 3-iodotetrahydrofuran which retains the free α-hydroxyl, using a protective group to protect said α-hydroxyl during a subsequent reaction to displace the iodine yielding the cis 3-hydroxytetrahydrofuran which upon deprotection and Swern oxidation provides the desired racemic (3-ketotetrahydrofuran-2-yl)ethanal.

4. A compound according to claim 1 wherein R is hydrogen.

* * * * *

UNITED STATES PATENT AND TRADEMARK OFFICE
CERTIFICATE OF CORRECTION

PATENT NO. : 5,684,166
DATED : Nov. 4, 1997
INVENTOR(S) : Hendry

It is certified that error appears in the above-identified patent and that said Letters Patent is hereby corrected as shown below:

On the title page, item [57], Abstract line 4,    "racetalc" should read --racemic--;
line 4-5, "rapresented" should read --represented--;
line 9,    "acylic" should read --acyclic--;
line 18,  "iodolaetonisation" should read --iodolactonisation--.

Column 3, line 63,    "triisopropylsilyl" should read --triisopropylsilyl chloride--.

Signed and Sealed this

Ninth Day of June, 1998

Attest:

BRUCE LEHMAN

Attesting Officer    Commissioner of Patents and Trademarks